(12) United States Patent
Lalonde

(10) Patent No.: US 7,955,274 B2
(45) Date of Patent: Jun. 7, 2011

(54) DEVICE FOR SIZING A HUMAN FEMALE BREAST

(75) Inventor: Donald H. Lalonde, Saint John (CA)

(73) Assignee: Accurate Surgical & Scientific Instruments Corporation, Westbury, NY (US)

( * ) Notice: Subject to any disclaimer, the term of this patent is extended or adjusted under 35 U.S.C. 154(b) by 359 days.

(21) Appl. No.: 11/512,686

(22) Filed: Aug. 30, 2006

(65) Prior Publication Data

US 2008/0125675 A1    May 29, 2008

(51) Int. Cl.
*A61B 5/103* (2006.01)
(52) U.S. Cl. ............................................ 600/587; 623/8
(58) Field of Classification Search .................. 600/587; 623/8
See application file for complete search history.

(56) References Cited

U.S. PATENT DOCUMENTS

| | | | | |
|---|---|---|---|---|
| 981,805 | A | * | 1/1911 | Smith .............................. 99/323 |
| 5,772,654 | A | * | 6/1998 | Leyva ................................. 606/1 |
| 5,951,365 | A | * | 9/1999 | Fildan ............................. 450/41 |
| 7,424,139 | B1 | * | 9/2008 | Stefan et al. .................. 382/128 |
| 2003/0216750 | A1 | * | 11/2003 | Wong ............................ 606/130 |
| 2004/0073106 | A1 | * | 4/2004 | Lee et al. ....................... 600/415 |
| 2006/0136069 | A1 | * | 6/2006 | Francalacci Franca .... 623/23.67 |

* cited by examiner

*Primary Examiner* — Max Hindenburg
*Assistant Examiner* — Renee Danega
(74) *Attorney, Agent, or Firm* — Jordan and Hamburg LLP

(57) ABSTRACT

A device for intraoperative sizing of a human female breast during resizing and/or shaping of the breast composes: a (a) substantially hemispherical, rigid, cup-shaped foraminous body, i.e., a foraminous cup, defining a desired size and shape of the breast; and (b) a rim member to which the foraminous cup is affixed.

5 Claims, 2 Drawing Sheets

DEVICE FOR SIZING A HUMAN FEMALE BREAST

BACKGROUND OF THE INVENTION

This invention relates to a device or set (plurality) of similar devices for sizing a human female breast. In particular, the invention relates to a device or plurality of similar devices for assisting achieving desired sizing of a human female breast in connection with surgery for increasing or decreasing the size of the breast.

There are numerous surgeries on human female breasts, some due to medical conditions such as removal of tumors and others for cosmetic purposes. The procedures variously involve increasing or reducing breast size and/or breast reshaping. These procedures include breast reduction, breast reconstruction, mastectomy and correcting asymmetry of breasts relative to each other. Heretofore, surgeries have not conducted rigorous intraoperative measurement of breasts upon which they are operating. Rather, the surgeries have estimated breast size and/or breast shape intraoperatively by eye and/or by cupping a hand over the breast. Such breast size and/or shape estimations are inherently imprecise.

It is an object of the invention to provide a device for intraoperative breast measurement in order to attain more precise breast sizing and shaping intraoperatively. It is a further object of the invention to provide devices functioning as breast sizers, by the use of which at various stages during an operation, the volumes of both breasts in the sizers are compared so that the breasts will end up as close as possible to the same size.

Other objects and advantages of the invention will be apparent from the following description of the invention.

SUMMARY OF THE INVENTION

According to the invention, there is provided a device for assisting in achieving the desired resizing or reshaping of a human female breast in connection with surgery in which the breast is increased or decreased in size and/or reshaped. The device comprises a substantially hemispherical, rigid, foraminous cup-shaped body defining a desired size and shape of the breast and a circular rim member to which the foraminous body is affixed.

In order that the surgeon's view of the breast being operated upon be obstructed as little as possible, the cup is to be of a very open construction. To that end, the cup preferably is made of a plurality of intersecting wires forming a wire network. Preferably, the wire network is constructed of two sets of intersecting wires, the wires of each set being substantially parallel to one another and one of the sets of wires intersecting the other set of wires substantially orthogonally and/or obliquely.

Preferably, the wires of one of the sets overlie the wires of the other set. It is also preferred that the wires are affixed to each other at the intersection thereof. Such affixation may be means of soldering, welding, adhesive or the like.

To the end of achieving an open construction so that the surgeon's view of the breast is minimally obstructed while the breast is received in the cup, a ratio of the average distance between adjacent parallel wires to the diameter of the same wires (based on all the wires being of substantially the same diameter) is preferably about 10:1 to about 600:1 and more preferably about 50:1 to about 400:1. A consideration defining upper limits of the ratio is that the wires not be so widely spaced as not to fully define the desired cup-shape and/or as not to sufficiently retain the breast. The diameter of the wires is preferably about 0.5 to about 2.5 millimeters and more preferably about 1 to about 1.5 millimeters. The wires should be relatively thin to reduce weight and expense of the device and contribute to less visual obstruction but not so thin that the cup is not rigid, i.e., retains its shape during the use for which is it intended and normal handling thereof by the surgical team or so thin that it would readily cut tissue.

The cup, i.e., cup-shaped foraminous body, is characterized herein as "substantially hemispherical". The word "substantially" is used because the cup is neither preferably nor necessarily an exact hemisphere but there is no other suitable geometric term. For example, the wall of the cup may be steeper near the rim than the wall of a precise hemisphere so that the cup, which being "substantially hemispherical", has somewhat the appearance of ceratin domes, for which, however, there is no precise geometrical term. Another departure from precisely hemispherical is that the hemisphere of the cup may be slightly less than 180°, for example, about 165° or 170° or greater but less than 180°. Such embodiments, too, are to be considered "substantially hemispherical" in the present invention.

Because the devices of the invention are surgical implements, a preferred material for the wires and the rim is stainless steel.

Breast sizes of women are generally indicated as cup sizes of brassieres. The most common brassier cup sizes, in ascending order, are "A", "B", "C" and "D". There are no precise standards for these cup sizes though they are generally similar from manufacture to manufacturer as are other garment sizes.

A surgeon regularly conducting breast surgeries may wish to have a set of devices of the present invention of different cup sizes to meet the requirements of various patients. The set may consist of two or more of the devices. The most generally useful set would be "A", "B" and "C" though a larger or smaller set is also within the scope of the present invention.

The device of the invention permits the intraoperative approximate volume measurement of breast pedicles or entire breasts. In breast surgeries, the skin overlying the breast may be peeled away. Surgeons refer to the breast without the skin as a "breast pedicle". The term "breast" as used herein means either a breast or a breast pedicle. A primary purpose of the invention is to assist the surgeon in assuring that both breasts are the same size.

To use the device of the present invention, the surgeon first selects an appropriately sized device of the invention and then manually manipulates the breast being operated upon into the device. The surgeon then firmly holds the rim of the device against an annular position of the patient's chest surrounding the breast to assure accuracy and so that his or her hands do not obstruct his or her view of the breast through the cup of the device. The breast can then be clearly seen by the surgeon and any volume of the device not filled by the breast will be obvious to the surgeon. The surgeon then uses the device on the other breast in the same way in order to compare the two breast volumes (and breast shapes), whereupon the surgeon can surgically adjust the size and/or configuration of the breast being operated upon if necessary to make the two breasts alike. (Of course, the measuring procedure may be repeated as necessary.)

The invention will now be further described by reference to specific exemplary embodiments as illustrated in the drawings and described hereinbelow.

DETAILED DESCRIPTION OF THE INVENTION

Figure 1:
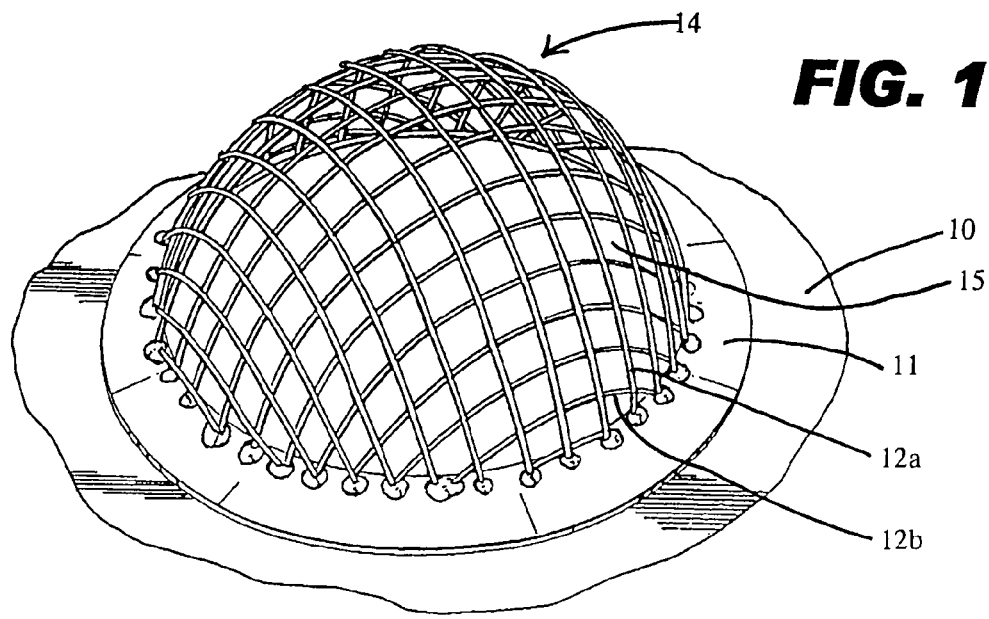
FIG. 1 is a perspective view of a device according to the invention.

A device 10 of the invention (FIG. 1) is constituted of a rim 11 to which, are fastened, for example by soldering, welding or adhesive, wires 12a and 12b. The wires 12a constitute one set of substantially parallel wires and the wires 12b constitute a second set of parallel wires. The wires 12b overlie the wires 11a to form a wire network. At their intersection 13, the wires 12a and 12b are fastened together, for example, by soldering, welding or adhesive. The wires 12a and 12b together constitute a cup-shape foraminous body ("cup") 14. The wires 12a and 12b are of 1 mm diameter. Adjacent wires of the set of wires 12a and adjacent wires of the set of wires 12b are spaced apart by 1 cm (10 mm).

Because the cup 14 is hemispherical, whereas wires of one set of wires 12a intersect wires of the other set of wires substantially orthogonally at some intersection, the wires intersect at various oblique angles at other intersections. Nevertheless, most of the spaces 15 bounded by the adjacent wires 12a, 12a and 12b, 12b of each of the sets of wires are of about the same area so that the area of any one such space is approximately the average area of the spaces. Moreover, most of the spaces are substantially square. It is, therefore, a simple arithmetic matter to conclude that the area of the average space is about 1 cm$^2$, i.e., 100 mm$^2$. Thus, in the specific embodiment illustrated in FIG. 1, the ratio of the average areas of the spaces 15 expressed in mm to the diameter of the wires 12a and 12b expressed in mm is 100, resulting in a construction of the cup 14 which provides the surgeon with a scarcely obstructed view of the breast being operated upon. Since the device is being used intraoperatively, typically areas of skin on the breast will have been peeled away, and, for example, in a breast reduction operation, the surgeon can see where it may be necessary to remove additional tissue.

Figure 4:
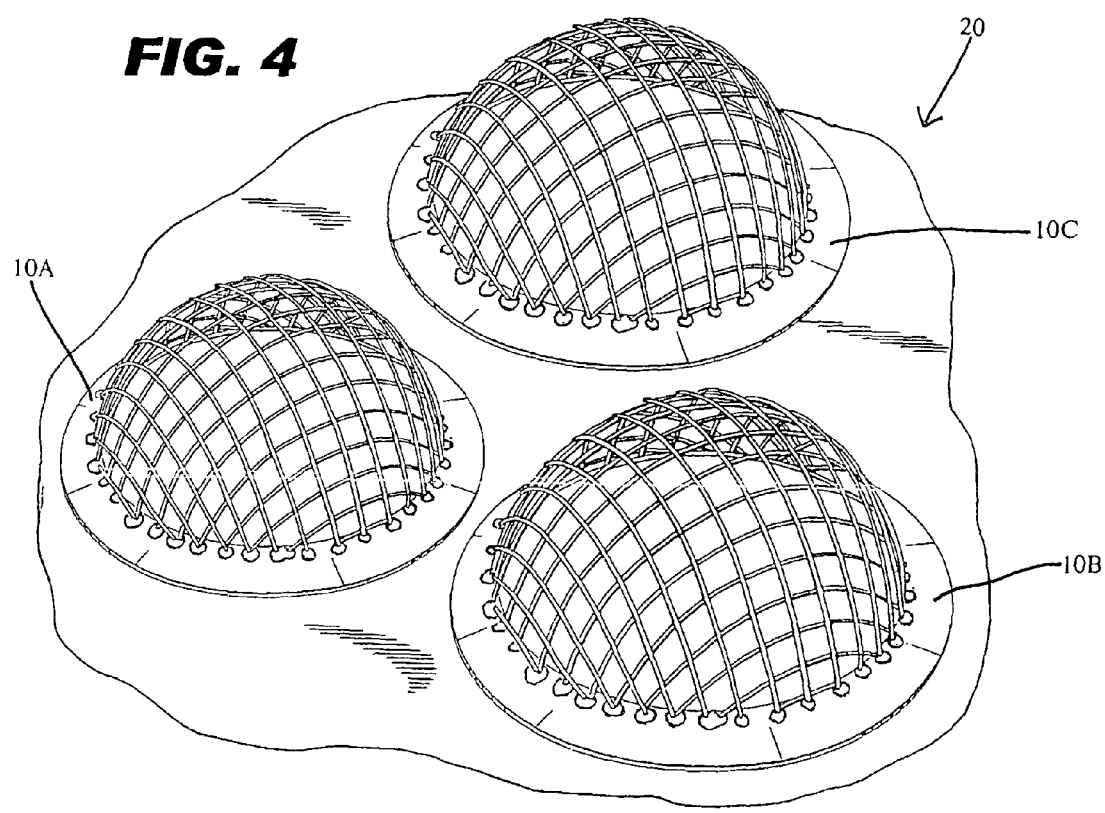
FIG. 4 is a perspective view of a set of devices according to the invention.

In FIG. 4 is illustrated an embodiment of the invention comprised of a set 20 of three of the devices of FIG. 1. The set consists of devices 10A, 10B and 10C of respective cup sizes "A", "B" and "C", which are of respective volumes about 250 cc, 375 cc and 500 cc. (A cup of size "D" would, consistent with this set, be of volume about 625 cc.) Furthermore, it is to be understood that the invention is not limited to cup sizes of designators "A", "B", "C" and "D" but can conform with any sequential order of cup sizes having prescribed volumes, such as "1", "2", "3", "4", etc. Such a set would be found highly useful by a surgeon who regularly performs breast operations of types such as those referred to hereinabove.

Figure 2:
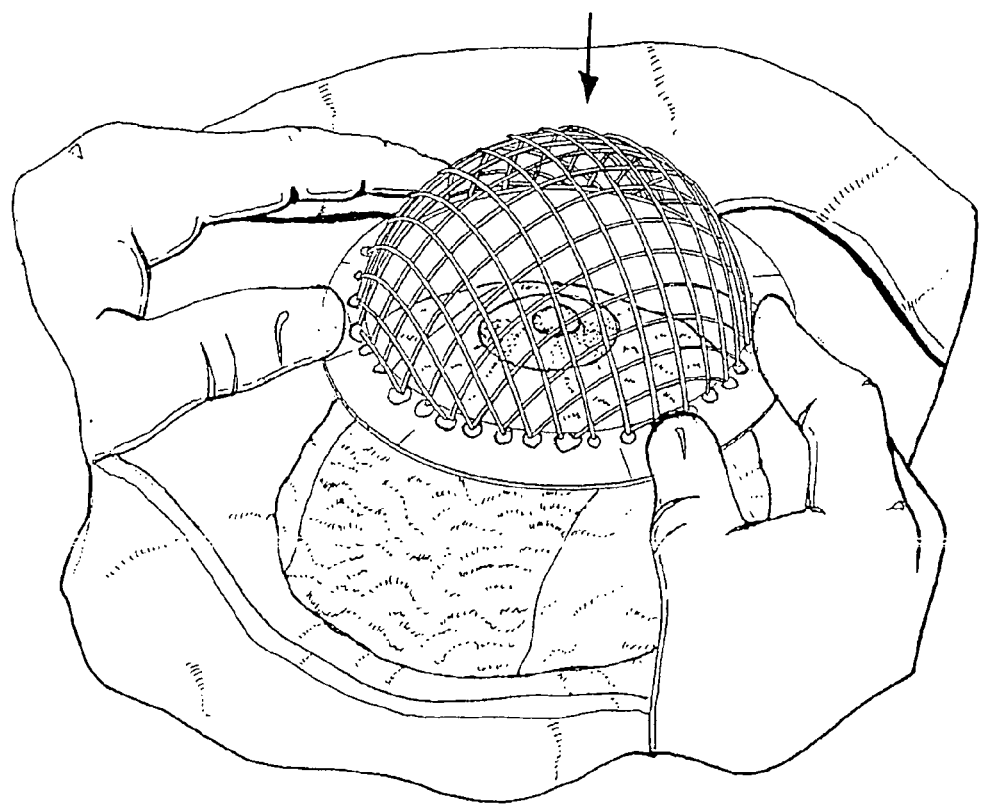
FIG. 2 is a perspective view of the application of the inventive device.
Figure 3:
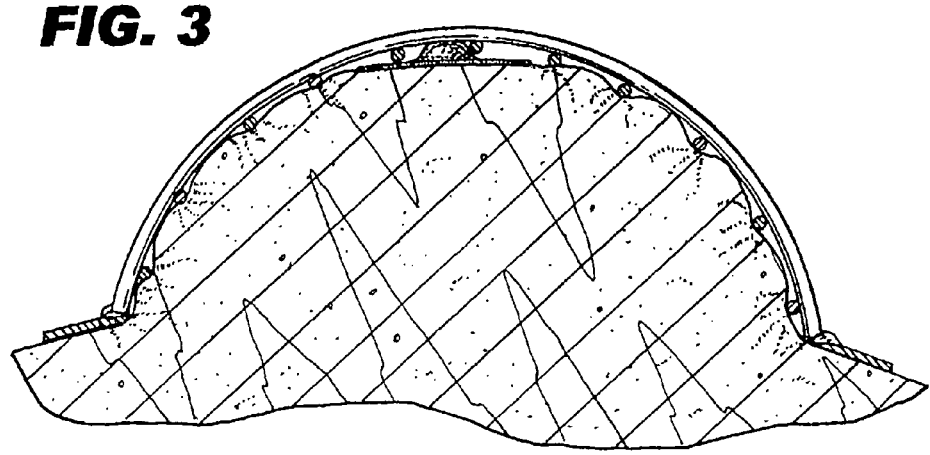
FIG. 3 is a cross sectional view of th device as positioned over a breast.

Turning now to FIGS. 2 and 3, there is illustrated a method of shaping a breast using the device of the invention. For example, with a breast reduction treatment, the nipple is moved into new position and excess skin and tissue are removed. The blood supply to the nipple is retained on a pedicle of tissue.

As the excess tissue is removed, the surgeon places the foraminous cup over the breast to assure that the volume of the breast precisely matches the volume within the cup. The spaced areas exposed by the wire network in the cup provide the surgeon with instant and dynamic visual confirmation that the remaining tissue mass has the correct volume and shape. With this visual confirmation, the surgeon can remove the cup, modify the remaining tissue and reapply the cup in an iterative pattern to quickly and accurately provide a breast having the desired shape and size.

While the invention has been described with respect to particular details thereof, it is to be understood that equivalents thereof are to be considered within the scope of the hereto appended claims.

The invention claimed is:

1. A method of resizing a human female breast, comprising:

obtaining a substantially hemispherical, rigid, cup-shaped foraminous body defining a desired size and/or shape of the breast, said body comprising an annular rim member wherein the foraminous body is affixed to the annular rim member, said foraminous body being configured such that the breast is viewable in relation to the foraminous body by visual observation through the foraminous body from an exterior thereof;

exposing a pedicle of the tissue of the breast to be resized and/or reshaped during an operation;

resizing and/or reshaping the breast; and positioning said cup-shaped foraminous body over the breast to determine if the size and/or shape of the breast matches the size and/or shape within the cup-shaped foraminous body by the visual observation from the exterior of the foraminous body;

if the size and/or shape of the breast differs from the size and/or shape within the cup-shaped foraminous body, removing said cup-shaped foraminous body from the breast, and continuing said resizing and/or reshaping the breast to revise a size and/or a reshaped outcome during said operation; and repositioning said cup-shaped foraminous body over the breast to determine if the size and/or shape of the breast matches the size and/or shape within the cup-shaped foraminous body by repeating the visual observation from the exterior of the foraminous body.

2. The method of claim 1 further comprising positioning said cup-shaped foraminous body over the other breast of the female for comparing the two breast sizes, and iteratively adjusting the size of the breast being operated upon so that the breast being operated upon is provided with the same size as the other breast.

3. A method of gauging a desired resizing and/or reshaping a human female breast of a patient and compensating for deviations therefrom intraoperatively, comprising:

selecting a device including a substantially hemispherical grating defining a concave receiving space within which the breast is receivable having a cup size and/or shape representative of a desired breast size and/or shape to be achieved, said hemispherical grating being configured such that the breast is viewable in relation to the hemispherical grating which represents the desired breast size and/or shape by visual observation through the hemispherical grating from an exterior of the device;

positioning said device with the breast received within the concave receiving space to determine if a size and/or a shape of the breast matches said cup size and/or shape by the visual observation from the exterior of the device;

removing said device from the breast if the size and/or shape of the breast differs from the cup size and/or shape;

resizing and/or re-shaping the breast; and repositioning said device with the breast once again received within the concave receiving space to determine, by repeating the visual observation from the exterior of the device, if a resized size and/or a resized shape of the breast matches the cup size and/or shape.

4. A method according to claim 3, further comprising:
repeating said positioning, said removing said device from the breast, said resizing and/or re-shaping the breast, and said repositioning, at least once, if said resized size and/or said resized shape of the breast fails to match the cup size and/or shape in said repositioning.

5. A method according to claim 3, further comprising positioning said device with an other breast of the patient received within the concave receiving space for comparing the size and/or shape of the breast to a corresponding size and/or shape of said other breast, and iteratively adjusting the size and/or shape of the breast and/or the other breast being operated upon so that the breast and/or the other breast being operated upon is provided with the same size as one another.

* * * * *